(12) United States Patent
Safadi

(10) Patent No.: US 12,234,269 B2
(45) Date of Patent: *Feb. 25, 2025

(54) OSTEOGENIC BIOMATERIAL

(71) Applicant: Northeast Ohio Medical University, Rootstown, OH (US)

(72) Inventor: Fayez Safadi, Akron, OH (US)

(73) Assignee: Northeast Ohio Medical University, Rootstown, OH (US)

( * ) Notice: Subject to any disclaimer, the term of this patent is extended or adjusted under 35 U.S.C. 154(b) by 91 days.

This patent is subject to a terminal disclaimer.

(21) Appl. No.: 17/340,405

(22) Filed: Jun. 7, 2021

(65) Prior Publication Data

US 2021/0300980 A1 Sep. 30, 2021

Related U.S. Application Data

(63) Continuation of application No. 15/512,964, filed as application No. PCT/US2015/051349 on Sep. 22, 2015, now Pat. No. 11,028,140.

(60) Provisional application No. 62/053,445, filed on Sep. 22, 2014.

(51) Int. Cl.
| | | |
|---|---|---|
| A61K 9/00 | (2006.01) | |
| A61K 31/00 | (2006.01) | |
| A61K 38/17 | (2006.01) | |
| A61K 47/36 | (2006.01) | |
| A61L 24/00 | (2006.01) | |
| A61L 27/24 | (2006.01) | |
| A61L 27/54 | (2006.01) | |
| A61L 27/58 | (2006.01) | |
| A61L 31/14 | (2006.01) | |
| A61L 31/16 | (2006.01) | |
| A61P 19/00 | (2006.01) | |
| C07K 14/51 | (2006.01) | |
| A61F 2/30 | (2006.01) | |
| A61K 47/34 | (2017.01) | |

(52) U.S. Cl.
CPC ............ *C07K 14/51* (2013.01); *A61K 9/0024* (2013.01); *A61K 38/1709* (2013.01); *A61K 47/36* (2013.01); *A61L 24/0015* (2013.01); *A61L 24/0042* (2013.01); *A61L 27/24* (2013.01); *A61L 27/54* (2013.01); *A61L 27/58* (2013.01); *A61L 31/148* (2013.01); *A61L 31/16* (2013.01); *A61F 2002/30062* (2013.01); *A61K 31/00* (2013.01); *A61K 47/34* (2013.01); *A61L 2300/25* (2013.01); *A61L 2300/412* (2013.01); *A61L 2430/02* (2013.01); *C07K 2319/00* (2013.01)

(58) Field of Classification Search
CPC .. C07K 14/51; A61K 9/0024; A61K 38/1709; A61K 47/36; A61K 31/00; A61L 24/0015; A61L 24/0042; A61L 27/54; A61L 27/58; A61L 31/149; A61L 31/16; A61L 2300/25; A61L 2430/02; A61P 19/00

See application file for complete search history.

(56) References Cited

U.S. PATENT DOCUMENTS

| | | | | |
|---|---|---|---|---|
| 4,703,108 | A ‡ | 10/1987 | Silver ...................... | A61K 9/70 128/DIG. 8 |
| 11,028,140 | B2 * | 6/2021 | Safadi ..................... | A61L 27/24 |
| 2002/0151486 | A1 ‡ | 10/2002 | Popoff ................ | A61K 38/1709 435/69.1 |
| 2005/0196772 | A1 ‡ | 9/2005 | Popoff ................ | A61K 38/1709 435/6.13 |
| 2006/0094679 | A1 ‡ | 5/2006 | Tsubouchi .............. | A61P 35/00 514/44 R |

FOREIGN PATENT DOCUMENTS

| | | | |
|---|---|---|---|
| WO | WO-02/062947 A2 | ‡ | 8/2002 |
| WO | WO-2012/158169 A1 | ‡ | 11/2012 |

OTHER PUBLICATIONS

Acarturk, Tahsin Oguz, and Jeffrey O. Hollinger. "Commercially available demineralized bone matrix compositions to regenerate calvarial critical-sized bone defects." Plastic and reconstructive surgery 118.4 (2006): 862-873. (Year: 2006).*
Li, Xian, et al. "Synthesis of radial mesoporous bioactive glass particles to deliver osteoactivin gene." Journal of Materials Chemistry B 2.40 (2014): 7045-7054. (Year: 2014).*
Katuri, Kishore Kumar, et al. "Evaluation of bioactive glass and demineralized freeze dried bone allograft in the treatment of periodontal intraosseous defects: A comparative clinico-radiographic study." Journal of Indian Society of Periodontology 17.3 (2013) : 367-372. (Year: 2013).*
Thibault, Richard A., Antonios G. Mikos, and F. Kurtis Kasper. "Scaffold/extracellular matrix hybrid constructs for bone-tissue engineering." Advanced healthcare materials 2.1 (2013): 13-24. (Year: 2013).*
Hu, Xuefeng, et al. "GPNMB enhances bone regeneration by promoting angiogenesis and osteogenesis: potential role for tissue engineering bone." Journal of cellular biochemistry 114.12 (2013): 2729-2737. (Year: 2013).*
Osteoactivin/GPNMB products, obtained online at https://www.rndsystems.com/target/osteoactivin-gpnmb, downloaded on Mar. 27, 2024.*

(Continued)

*Primary Examiner* — Abigail Vanhorn
(74) *Attorney, Agent, or Firm* — Tarolli, Sundheim, Covell & Tummino LLP

(57) ABSTRACT

A composition for enhancing bone tissue repair or regeneration is described. The composition includes osteoactivin or an active peptide fragment thereof and a biocompatible material. Osteogenic orthopedic devices including the osteoactivin-containing composition are also described. The devices and compositions can be used in methods for enhancing bone tissue repair or regeneration by contacting a site in need of bone repair or regeneration in a subject with the osteoactivin-containing composition.

11 Claims, 3 Drawing Sheets

Specification includes a Sequence Listing.

(56) References Cited

OTHER PUBLICATIONS

Stinnett, Hilary M., "Osteoactivin in Skeleton: Characterization of Osteoactivin Knockout Mice & Therapeutic Implications", A Dissertation Submitted to Kent State University in partial fulfillment of the requirements for the degree of Doctor of Philosophy, May 2015.‡
Bateman et al.; Exploratory study on the effect osteoactivin on bone formation in the rat critical-size calvarial defect model; Journal of Periodontal Research, 2012, pp. 243-247.‡
Hu et al.; GPNMB Enhances Bone Regeneration by Promoting Angiogenesis and Osteogenesis: Potential Role for Tissue Engineering Bone; Journal of Cellular Biochemistry, 2013, pp. 2729-2737.‡
International Search Report and Written Opinion for corresponding PCT Application No. PCT/US2015/051349.‡
Hoare et al., Polymer, 49, pp. 1993-2007. (Year: 2008).‡
Selim, The Role of Osteoactivin and Osteoactivin-Derived Peptides in Osteoblast Differentiation, Temple University Doctoral Disseration, pp. 1-109. (Year: 2004).‡
Vo et al., Adv Drug Deliv Rev., 64(12), pp. 1292-1309. (Year: 2012).‡
Selim, "The role of osteoactivin-derived peptides in osteoblast differentiation", Temple University Doctoral Dissertation, pp. 1-109 (2004).
Hoare et al., "Polymer", vol. 49 pp. 1993-2007 (2008).
Vo et al., "Strategies for Controlled Delivery of Growth Factors and Cells for Bone Regeneration" Advanced drug delivery reviews vol. 64, 12 (2012), pp. 1292-1309. doi: 10.1016/j.addr.2012.01.016.

\* cited by examiner
‡ imported from a related application

SEQUENCE LISTING

```
<160> NUMBER OF SEQ ID NOS: 1

<210> SEQ ID NO 1
<211> LENGTH: 18
<212> TYPE: PRT
<213> ORGANISM: Homo sapiens

<400> SEQUENCE: 1

Leu Ala Pro Phe Ser Arg Gly Asp Arg Glu Lys Asp Pro Leu Leu Gln
1               5                   10                  15

Asp Lys
```

OSTEOGENIC BIOMATERIAL

CROSS-REFERENCE TO RELATED APPLICATIONS

The present application is a continuation of U.S. patent application Ser. No. 15/512,964, which was a U.S. National Stage Application filed under 35 USC 371 and claiming priority to PCT Serial No. PCT/US2015/51349, filed on Sep. 22, 2015, which claims priority from U.S. Provisional Application Ser. No. 62/053,445, filed on Sep. 22, 2014, all of which are incorporated herein by reference.

GOVERNMENT FUNDING

This invention was made with government support under AR048892 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 10, 2023, is named NEO-023557_US_CON_1_SL.txt and is 585 bytes in size.

BACKGROUND

The search for osteoinductive therapeutic compounds remains critical to help accelerate bone healing in the case of major bone trauma, osteoporotic fractures, fusion surgeries, delayed or nonunions, revision prosthetic surgeries, and several oncology cases. Autologous bone grafting is most commonly used for the treatment of these cases and as such is the second most frequent tissue transplantation worldwide, second only to blood transfusions, with over 2 million bone grafting procedures performed each year worldwide.

Numerous biomaterials are available for bone grafts in oral and maxillo-facial surgery. They include autografts, allografts, xenografts and a wide variety of synthetic materials. Autografts are often referred to as the "gold standard"; bone is usually harvested from a donor site such as the iliac crest. Autogenous bone possesses all the characteristics necessary for producing new bone; it is osteogenic, osteoconductive and osteoinductive. Success rates are high but one obvious drawback of the autograft is the associated morbidity, including the possibility of recurrent pain, risk of infection, cost of a second surgery and the fact that autogenous bone is not always available in sufficient quantity or acceptable quality.

An alternate solution is to use an allograft, available from bone banks. In addition to the reluctance of many patients to having bone harvested from human cadavers grafted in their own body, the associated risks are still unclear. Despite the stringent preparation guidelines and rigorous donor screenings, the risk of human immunodeficiency virus (HIV) transmission alone with allograft bone is 1 case in 1.6 million population. Boyce et al., Orthop Clin North Am, 30, 571-581 (1999). A case of hepatitis B transmission and three cases of hepatitis C transmission have been reported with allograft tissue. Tomford W W, J Bone Joint Surg Am, 77, 1742-1754 (1995); Conrad et al., J Bone Joint Surg Am., 77, 214-224 (1995). Reports from the Center for Disease Control and Prevention revealed more recently that other diseases have been transmitted via allografts. Transmission of the much-feared Creutzfeldt-Jakob disease cannot be entirely excluded. Several allografts products were recalled in 2005 by the Food and Drug Administration. Another problem with the use of allografts is that the infection control and sterilization procedures greatly reduce the osteoinductivity of the bone tissue.

One way to avoid some of the drawbacks of the bone graft materials described above is to use synthetic biomaterials such as ceramic composites or ceramic/polymer composites. Ceramic composites include calcium sulfate cements, calcium phosphate-based sintered ceramics and cements, and bioactive glasses and glass-ceramics. Calcium phosphates have been studied extensively and used as synthetic bone graft materials. LeGeros et al., "Bioceramics: Calcium phosphate ceramics: past, present and future", Trans Tech Publications, Ben-Nissan B, ed.; Sydney, p 3-10 (2002). The most popular calcium phosphates used as bone graft materials are beta tricalcium phosphate (β-TCP) and hydroxyapatite (HAp), which can be either entirely synthetic or of coralline origin. β-TCP has been shown to have a higher resorption rate than HAp, which could lead to failure of the bone graft if this rate exceeds the rate at which new bone can be formed. Koerten et al., J Biomed Mater Res., 44, 78-86 (1999) Both β-TCP and HAp are mostly used in particle form or as coatings due to the difficulty of sintering in bulk form, together with the thermal instability of both ceramics. Another drawback of calcium phosphate ceramics lies in their mediocre mechanical properties, compared to both cancellous and cortical bone. Rezwan et al., Biomaterials, 27, 3413-3431 (2006).

Rather than relying on a bone graft, there are a number of advantages associated with stimulating existing bone to repair itself. Several models have been introduced and well documented to study osteoinductive compounds and biomaterials in bone healing. Osteoactivin (OA) is an osteoinductive protein encoded by the GPNMB gene that has been shown to stimulate osteoblast differentiation and function in vitro and bone regeneration in vivo. It has been shown that OA mRNA and protein are both highly expressed in osteoblasts in intact long bone and growth plate, and in fracture calluses collected at several time points during bone repair. Abdelmagic et al., J. Cell Biochem. 111, 295-309 (2010). Research has also indicated that mesenchymal stem cells, which are important for bone regeneration, displayed higher osteogenic differentiation when stimulated by OA. Raynaud et al., Stem Cells Int., 2012, I.D. 658356 (2012). OA has also been shown to support bone regeneration using an established bone defect model, where 70 percent of animals receiving osteoactivin showed complete bone fill, in comparison with control animals in which none of the animals exhibited complete bone fill at 4 weeks. Bateman et al., J. Periodontal Res. 47, 243-7 (2012). Finally, mutation of OA has been shown to result in a decrease in bone formation in vivo, and in osteoblast differentiation in vivo. Abdelmagid et al., Am J. Pathol. 184, 697-713 (2014). However, there remains a need for compositions and methods for delivering osteoactivin at sites in need of bone repair.

SUMMARY OF THE INVENTION

In one aspect, the present invention provides a composition for enhancing bone tissue repair or regeneration, comprising osteoactivin or an active peptide fragment thereof, and a biocompatible material. In some embodiments, the biocompatible material is a polymer, while in further embodiments the biocompatible material is a biodegradable polymer. In some embodiments, the osteoactivin or active peptide fragment thereof is covalently bound to the polymer.

In yet further embodiments, the biocompatible material is configured as a tissue scaffold. In additional embodiments, the biocompatible material is selected from the group consisting of an allograft, a demineralized bone matrix, collagen, chitosan, a xenograft, and silicate or silicate derived materials.

In another aspect, the present invention provides a method for enhancing bone tissue repair or regeneration, comprising contacting a site in need of bone repair or regeneration in a subject with a composition comprising osteoactivin or an active peptide fragment thereof, and a biocompatible material. In some embodiments, the composition is in an injectable form, and the step of contacting the site comprises administering the composition by injection to the site in need of bone repair or regeneration. In other embodiments, the step of contacting the site comprises surgically implanting the composition. In further embodiments, the site in need of bone repair or regeneration is a dental site.

In some embodiments of the method, the biocompatible material is a polymer, while in further embodiments the biocompatible material is a biodegradable polymer. In some embodiments, the osteoactivin or active peptide fragment thereof is covalently bound to the polymer. In yet further embodiments, the biocompatible material is configured as a tissue scaffold. In additional embodiments, the biocompatible material is selected from the group consisting of an allograft, a demineralized bone matrix, collagen, chitosan, xenograft, and silicate or silicate derived materials.

Another aspect of the invention provides an osteogenic orthopedic device, comprising: An implantable orthopedic device, coated with a composition comprising osteoactivin or an active peptide fragment thereof, and a biocompatible material. In some embodiments, the orthopedic device is a bone fixation member having bone interfaces or outer bone contacting surfaces.

In further embodiments of the device, the biocompatible material is a polymer, while in other embodiments the biocompatible material is a biodegradable polymer. In some embodiments, the osteoactivin or active peptide fragment thereof is covalently bound to the polymer. In yet further embodiments, the biocompatible material is configured as a tissue scaffold. In additional embodiments, the biocompatible material is selected from the group consisting of an allograft, a demineralized bone matrix, collagen, chitosan, a xenograft, and silicate or silicate derived materials.

DETAILED DESCRIPTION OF THE INVENTION

Figure 1:
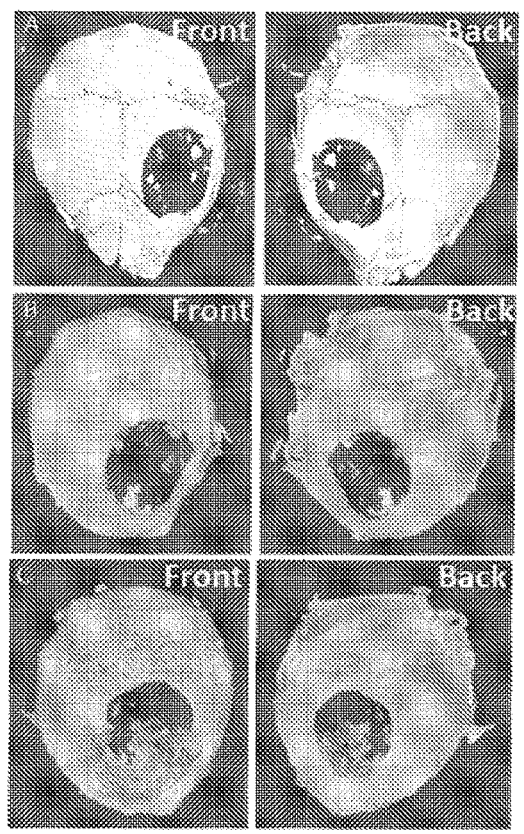
FIG. 1 provides images showing the effects of osteoactivin-derived peptide on bone regeneration. Three dimensional micro-computed topography (μCT) reconstruction analysis showed collagen sponge soaked osteoactivin-derived peptide (C) compared to defect only (A) or collagen sponge alone (B).

The present invention provides a composition for enhancing bone tissue repair or regeneration. The composition includes osteoactivin or an active peptide fragment thereof and a biocompatible material. Another aspect of the invention includes implantable orthopedic devices including the osteoactivin-containing composition. The devices and compositions can be used in methods for enhancing bone tissue repair or regeneration by contacting a site in need of bone repair or regeneration in a subject with the osteoactivin-containing composition.

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

Also herein, the recitations of numerical ranges by endpoints include all numbers subsumed within that range (e.g., 1 to 5 includes 1, 1.5, 2, 2.75, 3, 3.80, 4, 5, etc.).

A "subject," as used herein, can be any animal, and may also be referred to as the patient. Preferably the subject is a vertebrate animal, and more preferably the subject is a mammal, such as a research animal (e.g., a mouse or rat) or a domesticated farm animal (e.g., cow, horse, pig) or pet (e.g., dog, cat). In some embodiments, the subject is a human.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

"Biocompatible" as used herein, refers to any material that does not cause injury or death to a subject or induce an adverse reaction in a subject when placed in contact with the subject's tissues. Adverse reactions include for example inflammation, infection, fibrotic tissue formation, cell death, or thrombosis. The terms "biocompatible" and "biocompatibility" when used herein are art-recognized and mean that the material is neither itself toxic to a subject, nor degrades (if it degrades) at a rate that produces byproducts (e.g., monomeric or oligomeric subunits or other byproducts) at toxic concentrations, does not cause prolonged inflammation or irritation, or does not induce more than a basal immune reaction in the host.

As used herein, the terms "peptide," "polypeptide" and "protein" are used interchangeably, and refer to a compound comprised of amino acid residues covalently linked by peptide bonds. A protein or peptide must contain at least four amino acids, unless specified otherwise, and no limitation is placed on the maximum number of amino acids that can comprise the sequence of a protein or peptide. Polypeptides include any peptide or protein comprising four or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

Osteoactivin-Containing Biocompatible Materials

In one aspect, the invention provides a composition for enhancing bone tissue repair or regeneration. The composition includes osteoactivin or an active peptide fragment thereof, and a biocompatible material (a.k.a., an osteoactivin-containing composition). Typically, only a small percentage of the composition is osteoactivin. For example, the composition for enhancing bone tissue repair or regeneration can include up to 5%, up to 1%, or less than 1%, but greater than 0%, of osteoactivin. Preferably, a therapeutically effective amount of osteoactivin is included in the composition.

Osteoactivin is a 572 amino acid transmembrane glycoprotein, described by U.S. Pat. No. 6,812,002, the disclosure of which is incorporated by reference herein. The protein has a predicted molecular weight of 63.8 kD. Osteoactivin plays a role in osteoblast development, bone cell differentiation, and bone formation, and therefore is involved in normal skeletal modeling/remodeling. The human and mouse orthologues of osteoactivin are known as GPNMB and DC-HIL, respectively.

Osteoactivin proteins, peptide fragments thereof, mutants, truncations, derivatives, analogs, and splice variants that display substantially equivalent or altered osteoactivin activity relative to the wild-type protein are likewise contemplated for use in the present invention. These variants may be deliberate, for example, such as modifications obtained through site-directed mutagenesis, or may be accidental, such as those obtained through mutations in hosts that are producers of the osteoactivin protein. Included within the scope of these terms are osteoactivin proteins specifically recited herein, as well as all substantially homologous analogs and allelic variants.

Analogs may be made through substitution of conserved amino acids. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in an osteoactivin protein is preferably replaced with another amino acid residue from the same side chain family. Alternatively, in another embodiment, mutations can be introduced randomly along all or part of an osteoactivin coding sequence, such as by saturation mutagenesis, and the resultant mutants can be screened for osteoactivin biological activity to identify mutants that retain activity. Following mutagenesis of the nucleotide sequence for osteoactivin, the encoded protein can be expressed recombinantly and the activity of the protein can be determined.

A "non-essential" amino acid residue is a residue that can be altered from the wild-type sequence of osteoactivin without abolishing or, more preferably, without substantially altering a biological activity, whereas an "essential" amino acid residue results in such a change. For example, amino acid residues that are conserved among the polypeptides of the present invention are predicted to be particularly unamenable to alteration.

As used herein, an "active peptide fragment" of an osteoactivin protein includes a fragment of an osteoactivin protein that can modulate bone cell differentiation or stimulate bone formation. Biologically active portions of an osteoactivin protein include peptides comprising amino acid sequences sufficiently homologous to or derived from the amino acid sequence of an osteoactivin protein which include less amino acids than a full length osteoactivin proteins and which exhibit at least one activity of an osteoactivin protein. A biologically active portion of an osteoactivin protein can be a polypeptide which is, e.g., 6, 12, 18, 36, 72 or more amino acids in length.

A preferred osteoactivin active peptide fragment for use in the present invention is the amino acid sequence LAPFSRG-DREKDPLLQDK (SEQ ID NO: 1). The inventors have demonstrated the osteogenic activity of this peptide, and shorter amino acid fragments thereof. Accordingly, in some embodiments, shorter sections of SEQ ID NO: 1 consisting of 6 or 12 amino acids can be used.

The inventors have demonstrated that osteoactivin (OA) as a bone anabolic agent. It is synthesized and secreted by osteoblasts where it acts as signaling molecule to promote osteoblast differentiation and function. Local delivery of OA stimulates bone regeneration in a model of bone segmental defect, while systemic delivery of OA-derived peptide increases systemic bone mass. Research has also shown that OA is involved in mouse and human stem cells differentiation to bone cells, and that OA is responsible to transdifferentiate muscle cells to bone forming osteoblasts. The receptor for OA in bone and mesenchymal stem cells is CD44. OA induces differentiation of mesenchymal stem cells to bone cells through CD44.

OA expression is increased during bone regeneration in different model, fracture in rats and human, during socket bone formation after tooth extraction. During a Reamer-Irrigator-Aspirator (RIA) procedure in humans, where OA is used for healing large bone defect, OA is highly expressed in the RIA-water. RIA water is capable of inducing bone regeneration in a model of SCID mice.

Compositions of the present invention include osteoactivin and a biocompatible material. Suitable biocompatible materials include biocompatible polymers; graft materials such as an allograft or xenograft; bone-derived materials, collagen, and biocompatible inorganic materials. Examples of biocompatible polymers include polymers include natural or synthetic polymers such as polystyrene, polylactic acid, polyketal, butadiene styrene, styreneacrylic-vinyl terpolymer, polymethylmethacrylate, polyethylmethacrylate, polyalkylcyanoacrylate, styrene-maleic anhydride copolymer, polyvinyl acetate, polyvinylpyridine, polydivinylbenzene, polybutyleneterephthalate, acrylonitrile, vinylchloride-acrylates, polycaprolactone, poly(alkyl cyanoacrylates), poly(lactic-co-glycolic acid), and the like.

In some embodiments, the biocompatible material is an inorganic material, such as an inorganic ceramic and/or bone substitute material. Exemplary inorganic materials or bone substitute materials include but are not limited to aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, α-tricalcium phosphate, dicalcium phosphate, β-tricalcium phosphate, tetracalcium phosphate, amorphous calcium phosphate, octacalcium phosphate, BIOGLASS™, fluoroapatite, chlorapatite, magnesium-substituted tricalcium phosphate, carbonate hydroxyapatite, substituted forms of hydroxyapatite (e.g., hydroxyapatite derived from bone may be substituted with other ions such as fluoride, chloride, magnesium sodium, potassium, etc.), coral, silicate or silicate derived materials, or combinations or derivatives thereof.

In some embodiments, the biocompatible material may comprise particles of bone-derived materials. The bone-derived material may include one or more of non-demineralized bone particles, demineralized bone particles, lightly demineralized bone particles, and/or deorganified bone particles.

In some embodiments, the biocompatible material is a biodegradable polymer. Examples of biodegradable polymers include polylactide polymers include poly(D,L-Lactide)s; poly(lactide-co-glycolide) (PLGA) copolymers; polyglycolide (PGA) and polydioxanone; caprolactone polymers; chitosan; hydroxybutyric acids; polyanhydrides and polyesters; polyphosphazenes; and polyphosphoesters.

Functionalized poly(D,L-Lactide)s can also be used as biodegradable polymers in the nanoparticles of the invention. Examples of functionalized poly(D,L-Lactide)s include poly(L-lactide), acrylate terminated; poly(L-lactide), amine terminated; poly(L-lactide), azide terminated; poly(L-lactide), 2-bromoisobutyryl terminated; poly(L-lactide), 2-bromoisobutyryl terminated; poly(L-lactide) 4-cyano-4-[(dodecylsulfanylthiocarbonyl)sulfanyl]pentonate; poly(L-lactide) N-2-hydroxyethylmaleimide terminated; poly(L-lactide) 2-hydroxyethyl, methacrylate terminated; poly(L-lactide), propargyl terminated; poly(L-lactide), thiol terminated;

Other biodegradable polymers that can be used include AB diblock copolymers such as poly(ethylene glycol) methyl ether-block-poly(D,L lactide); poly(ethylene glycol) methyl ether-block-poly(lactide-co-glycolide) PEG; poly(ethylene glycol)-block-poly(ε-caprolactone) methyl ether PEG; and Polypyrrole-block-poly(caprolactone). Further biodegradable polymers include ABA triblock copolymers such as polylactide-block-poly(ethylene glycol)-block-polylactide PLA; poly(lactide-co-glycolide)-block-poly(ethylene glycol)-block-poly(lactide-co-glycolide); poly(lactide-co-caprolactone)-block-poly(ethylene glycol)-block-poly(lactide-co-caprolactone); polycaprolactone-block-polytetrahydrofuran-polycaprolactone; and polyglycolide-block-poly(ethylene glycol)-block-polyglycolide PEG.

Biodegradable polymers also include various natural polymers. Examples of natural polymers include polypeptides including those modified non-peptide components, such as saccharide chains and lipids; nucleotides; sugar-based biopolymers such as polysaccharides; cellulose; chitosan, carbohydrates and starches; dextrans; lignins; polyamino acids; adhesion proteins; lipids and phospholipids (e.g., phosphorylcholine).

In some embodiments, the biodegradable polymer is synthesized by step growth polymerization. Step growth polymerization of suitable monomers allows the components to be linked using milder conditions such as carbodiimide mediated polymerization that avoid possible degradation of the osteoactivin. Functionalization of these polymers with osteoactivin provides a polymer that will stimulate osteogenesis, and is therefore useful for encouraging bone tissue repair and regeneration.

Suitable monomers and reaction conditions are shown in Scheme 1, provided below. The monomers can be synthesized by appropriate synthetic methodologies, and osteoactivin or osteoactivin fragments can be incorporated into the monomers before polymerization. The polymers are synthesized by step growth polymerization using diisopropylcarbodiimide (DIC) and DPTX (complex of dimethylaminopyridine and p-toluene sulfonic acid) in $CH_2Cl_2$ or $CH_2Cl_2$/DMF for 24-48 hours. This methodology can be used to make random copolymers, alternating copolymers, and sequence specific polymers.

Scheme 1

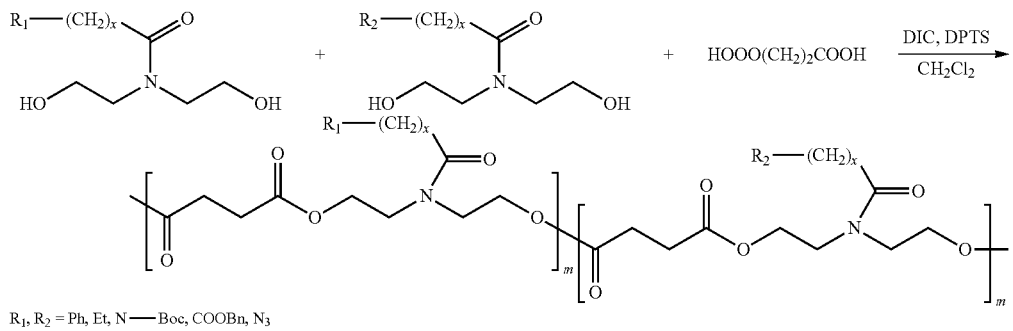

In further embodiments, the osteoactivin or active peptide fragment thereof is covalently bound to the polymer. The osteoactivin or active peptide fragment thereof can be coupled to the polymer either directly or indirectly (e.g. via a linker group). In some embodiments, the osteoactivin is covalently attached to a functional group capable of reacting with the osteoactivin. For example, a nucleophilic group, such as an amino or sulfhydryl group, can be capable of reacting with a carbonyl-containing group, such as an anhydride or an acid halide, or with an alkyl group containing a good leaving group (e.g., a halide). Alternatively, a suitable chemical linker group can be used. A linker group can serve to increase the chemical reactivity of a substituent on either the osteoactivin or the polymer, and thus increase the coupling efficiency.

In some embodiments, the osteoactivin may be disposed on or in the biocompatible material by hand, electrospraying, ionization spraying or impregnating, vibratory dispersion (including sonication), nozzle spraying, compressed-air-assisted spraying, brushing and/or pouring.

In some embodiments, the biocompatible material is configured as a tissue scaffold. A tissue scaffold is a support structure that provides a matrix for cells to guide the process of bone tissue formation in vivo. The morphology of the scaffold guides cell migration and cells are able to migrate into or over the scaffold, respectively. The cells then are able to proliferate and synthesize new tissue and form bone and/or cartilage. While there are many criteria for an ideal tissue scaffold for bone tissue repair, an important characteristic is the presence of a highly interconnected porous network with both pore sizes and pore interconnections large enough for cell migration, fluid exchange, and eventual tissue in-growth and vascularization.

The biocompatible material can be molded or otherwise shaped during preparation to have any desired configuration as a tissue scaffold. Typically, the biocompatible material is molded to have the shape of the bone or bone-like material that it is being substituted for. However, the scaffold material can also be used for cosmetic work or "bioengineering," where a support structure is provided for the creation of new tissue rather than the replacement or regeneration of existing tissue. In some embodiments, the tissue scaffold may be seeded with harvested bone cells and/or bone tissue, such as for example, cortical bone, autogenous bone, allogenic bones and/or xenogenic bone. For further information regarding suitable tissue scaffolds for bone repair or regeneration, see for example U.S. patent application Ser. Nos. 11/793,625, 12/193,794, 13/908,627, or 14/216,451, the disclosures of which are incorporated herein by reference.

In some embodiments, the scaffold is bioresorbable. Bioresorbable, as used herein, refers to the ability of the scaffolds to be gradually degraded by physiological processes in vivo, to allow the replacement of the biocompatible material with native tissue. For example, if the scaffold is used to replace bone, the scaffold may be gradually degraded while osteoblasts rebuild bone tissue in its place (i.e., bone remodeling).

The tissue scaffold can be prepared by a variety of methods, depending in part on the nature of the biocompatible material being used. For example, the tissue scaffold may be made by injection molding, compression molding, blow molding, thermoforming, die pressing, slip casting, electrochemical machining, laser cutting, water-jet machining, electrophoretic deposition, powder injection molding, sand casting, shell mold casting, lost tissue scaffold casting, plaster-mold casting, ceramic-mold casting, investment casting, vacuum casting, permanent-mold casting, slush casting, pressure casting, die casting, centrifugal casting, squeeze casting, rolling, forging, swaging, extrusion, shearing, spinning, powder metallurgy compaction or combinations thereof.

In some embodiments, the biocompatible material includes one or more additional growth factors, in addition to osteoactivin. These growth factors include osteoinductive agents (e.g., agents that cause new bone growth in an area where there was none) and/or osteoconductive agents (e.g., agents that cause in growth of cells into and/or through the tissue scaffold). Osteoinductive agents include, but are not limited to, isolated Bone Morphogenetic Protein (BMP), Vascular Endothelial Growth Factor (VEGF), Connective Tissue Growth Factor (CTGF), Osteoprotegerin, Growth Differentiation Factors (GDFs), Cartilage Derived Morphogenic Proteins (CDMPs), Lim Mineralization Proteins (LMPs), Platelet derived growth factor, (PDGF or rhPDGF), Insulin-like growth factor (IGF) and Transforming Growth Factor beta (TGF-β).

Osteoactivin-Containing Implantable Devices

Another aspect of the invention provides an osteogenic orthopedic device that includes an implantable orthopedic device, coated with a composition comprising osteoactivin or an active peptide fragment thereof, and a biocompatible material. An osteogenic orthopedic device is a device that promotes bone repair or regeneration upon implantation into a subject. The biocompatible material can be any of the biocompatible materials described herein, such as biocompatible polymers; graft materials such as an allograft or xenograft; bone-derived materials, collagen, and biocompatible inorganic materials. The coating of the osteoactivin-containing material can cover all or a portion of the implantable orthopedic device.

Orthopedic implants are commonly used to replace some or all of a patient's bone tissue or joint, such as a hip, knee, shoulder or elbow, where deterioration of or damage to the joint due to aging, illness, injury or trauma is present. These implants are designed to accommodate the normal movements and stresses associated with such joints and to provide increased mobility and relief from pain. When an orthopedic implant of the present invention is delivered to a site in need of bone repair or regeneration, it includes a coating of osteoactivin or an active peptide fragment thereof, and a biocompatible material, in order to stimulate enhanced repair and regeneration of bone at the implant site in order to better integrate the implant with adjacent bone tissue.

Orthopedic devices can be shaped to replace all or a part of any bone, including long bones, short bones, flat bones, irregular bones and sesmoid bones. Orthopedic implants can be formed from biocompatible metals such as titanium, tungsten, or chromium, as well as biocompatible polymers; graft materials such as an allograft or xenograft; bone-derived materials, collagen, and biocompatible inorganic materials. Orthopedic implants can have a wide variety of different shapes, depending on the bone or bone section they are designed to replace. See for example U.S. patent application Ser. No. 14/455,524, which describes a wide variety of orthopedic implants that can be manufactured through use of a 3D model, the disclosure of which is incorporated herein by reference.

In some embodiments, the orthopedic device also a bone fixation member having bone interfaces or outer bone contacting surfaces. Preferably the bone fixation member has bone contacting surfaces that are porous and allow for bone tissue ingrowth from the adjacent natural bone. Examples of suitable bone fixation members are described by U.S. patent application Ser. Nos. 12/963,858, 13/800,319, and 13/884,171, the disclosures of which are incorporated herein by reference.

Methods for Enhancing Bone Tissue Repair or Regeneration

Another aspect of the invention provides method for enhancing bone tissue repair or regeneration that includes contacting a site in need of bone repair or regeneration in a subject with a composition comprising osteoactivin or an active peptide fragment thereof, and a biocompatible material. The biocompatible material can include any of the biocompatible materials described herein, such as biocompatible polymers; graft materials such as an allograft or xenograft; bone-derived materials, collagen, and biocompatible inorganic materials.

The method for enhancing bone tissue repair or regeneration includes in vivo placement of an osteoactivin-containing composition, or an implantable orthopedic device coated with an osteoactivin-containing composition, as described herein for bioengineering, restoring or regenerating bone. In particular aspects of the method, bioengineering, restoring or regenerating bone is in vitro or ex vivo, including placement under body fluid conditions. The method includes positioning osteoactivin-containing composition, or an implantable orthopedic device coated with an osteoactivin-containing composition to provide structural support for nearby tissue. In particular embodiments of the method, the compositions are used for dental and orthopedic implants, craniomaxillofacial applications and spinal grafting, and said composition is suitable to promote bone regeneration and repair.

A bone (i.e., bone tissue) is a rigid organ that constitutes part of the vertebral skeleton. Bone tissue includes two basic types—cortical (the hard, outer layer of bone) and cancellous bone (the interior trabecular or spongy bone tissue), which gives it rigidity and a coral-like three-dimensional internal structure. Other types of tissue found in bone include marrow, endosteum, periosteum, nerves, blood vessels and cartilage. Bone is an active tissue composed of different cells. Osteoblasts are involved in the creation and mineralization of bone; osteocytes and osteoclasts are involved in the reabsorption of bone tissue. The mineralized matrix of bone tissue has an organic component mainly of collagen and an inorganic component of bone mineral made up of various salts.

The present invention can be used to repair or regenerate any type of bone. There are five types of bones in the human body. These are long bones, short bones, flat bones, irregular bones and sesmoid bones. Examples of long bones include the femur, the humerus and the tibia. Examples of short bones include carpals and tarsals in the wrist and foot. Examples of flat bones include the scapula, the sternum, the cranium, the os coxae, the pelvis, and ribs. Irregular bones are those which do not fit within the other categories, and include vertebrae, sacrum and mandible bones. Sesmoid bones are typically short or irregular bones, imbedded in a tendon, such as the patella. While not formally considered bone, teeth are also included in the definition of bone used herein.

The present invention provides compositions and methods for enhancing bone tissue repair or regeneration. The terms bone regeneration and repair are often used together or interchangeably by those skilled in the art with regard to skeletal reconstructive procedures. For an overview of bone repair and regeneration, see Panetta et al., the disclosure of which is incorporated herein by reference. Panetta et al., Curr Stem Cell Res Ther., 5(2), 122-8 (2010). More specifically, bone repair refers to treatment of a bone injury, while bone regeneration refers to the stimulation of the replacement of bone tissue by the body. Bone injury can occur as a result of disease, chronic stress, or physical trauma. Examples of different types of bone injury include degenerative disc, cervical spondylosis, and bone fracture. Bone regeneration is also called remodeling and occurs at the cellular level. When the process becomes unbalanced, bone mass decreases and bones may become brittle. Reference to enhancing bone regeneration by the present invention implies a rebalancing of bone remodeling in such a situation. Enhancing bone repair or regeneration refers to increasing bone repair or regeneration beyond what would normally occur in the absence of treatment using the present compositions and methods. Enhancing bone repair includes increasing the rate of bone repair and the amount of bone repair that occurs over a given time. For example, enhancing bone repair includes increasing the rate or amount of bone repair by 10%, 20%, 30%, 40%, 50%, 60%, 70%, 80%, 90%, 100%, 150%, 200%, or more compared with the amount or rate of bone repair or regeneration that would occur in an untreated subject.

Preferably the method of enhancing bone tissue repair or regeneration occurs under aseptic conditions. "Aseptic" as the term is used herein, refers to methods to control or reduce the microbial bioburden in an environment. Tissues processed "aseptically" are tissues processed using sterile instruments, and special environmental surroundings (including for example "clean room technologies").

Contacting, as used herein, refers to causing two items to become physically adjacent and in contact, or placing them in an environment where such contact will occur within a short timeframe. For example, contacting a site with a composition comprising osteoactivin and a biocompatible material includes administering the composition to s subject at or near a site such that the osteoactivin will interact with the site to stimulate enhanced bone repair or regeneration. In some embodiments, the step of contacting the site comprises surgically implanting the composition. Methods of surgically implanting orthopedic implants and biocompatible materials for bone repair and regeneration are known to those skilled in the art.

In some embodiments, the composition is in an injectable form, and the step of contacting the site comprises administering the composition by injection to the site in need of bone repair or regeneration. "Injectable" refers to the ability of certain osteoactivin-containing compositions of the present invention to be introduced at an implant site under pressure (as by introduction using a syringe). An injectable composition of the present invention may, for example, be introduced between elements or into a confined space in vivo (i.e., between pieces of bone or into the interface between a prosthetic device and bone, among others). For example, the compositions may be injected into the vertebral body for prevention or treatment of spinal fractures, injected into long bone or flat bone fractures to augment the fracture repair or to stabilize the fractured fragments, or injected into intact osteoporotic bones to improve bone strength.

Examples of injectable forms include a fluid injectable gel and a fluid injectable paste. A wide variety of flowable compositions suitable for injection are known to those skilled in the art, including various hydrogel compositions. See for example U.S. Pat. No. 8,309,106. Preferably, the injectable composition is extrudable through a syringe and/or a syringe having at least a 13 gauge tube/needle coupled thereto.

In further embodiments, the site in need of bone repair or regeneration is a dental site. Bone repair or regeneration conducted at a dental site can involve the repair of teeth, or bone tissue near the teeth. The osteoactivin-containing composition can be used as part of a bone repair process following extraction of a tooth and/or placement of a dental prosthesis, or for repairing dental bone defects such as bone loss from moderate or severe periodontitis.

The present invention is illustrated by the following examples. It is to be understood that the particular examples, materials, amounts, and procedures are to be interpreted broadly in accordance with the scope and spirit of the invention as set forth herein

EXAMPLES

Example 1: The Role of Osteoactivin in Bone Regeneration: A Sheep Model for Cancellous Bone Healing In order to demonstrate therapeutic efficacy of osteoactivin (OA) in bone regeneration, a larger animal model is important to predict the effect of the compound in humans. Thus, the sheep model provides a way to study the effect of OA on osteogenesis by inducing critical size defects into the long bones of the animals. In this study, we show that critical size defects introduced into bilateral distal femurs of a sheep (n=6) dosed with an OA-soaked absorbable collagen sponge had significantly accelerated bone healing and regeneration, characterized by radiographic, μCT imaging and histological analysis when compared to control sheep (defect only or collagen sponge treated alone).

Methods

Approval of the Northeast Ohio Medical University Institutional Animal Care and Use Committee (IACUC) was obtained prior to the start of this study. Six (6) male sheep (*Ovis aries*) between ages 2-3 years old were used, each with a critical size defect (25 mm in depth×11 mm in diameter) drilled into bilateral hind limb distal femurs. The surgical protocol utilized was based on previous work done to develop a model for cancellous bone healing (Malhotra et al, Front Surg. 2014 Sep. 8; 1:37). This method allowed for high quality standardization and sterility processes across each sheep. Furthermore, Martini et al., 2001 and Pearce et al, 2007 have demonstrated comparable rates of bone healing, bone turnover, and remodeling activity between sheep and humans. Martini et al., Comp Med. 2001 August; 51(4):292-9; Pearce et al., Eur Cell Mater. 2007 Mar. 2; 13:1-10. The procedures were performed by an orthopedic surgeon. Once under appropriate anesthesia, one femur defect (left hindlimb) was drilled with a cannulated acorn drill (Stryker) and packed with an PBS absorbable collagen sponge (Medline Industries) without OA protein and thus functioned as a control, while the other defect (right hindlimb) was filled with either a low dose (10 μg), or high dose (50 μg) recombinant OA-soaked collagen sponge (R&D Systems). Three sheep received the high dose OA while two received the low dose OA, and one was left as a control. The animals were allowed to recover and then terminated after a period of 10 weeks. The femurs were harvested for x-ray (General Electric) and μCT (Scanco) imaging. Blood and urine samples were collected for CBC, CMP and urinalysis (ANTECH Diagnostics). Tissue biopsies were taken from heart, lung, liver, spleen, kidney, thyroid gland, adrenal gland, and skeletal muscle for RNA and histological analyses during post-mortem dissection.

Results

Figure 2A:
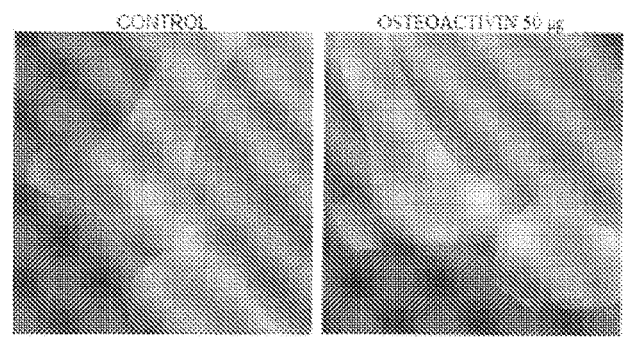
FIG. 2(A, B) provides (A) radiographs and (B) μCT showing 50 μg OA-treated femur with regenerated bone after 10 weeks compared to control in defect site.
Figure 2B:
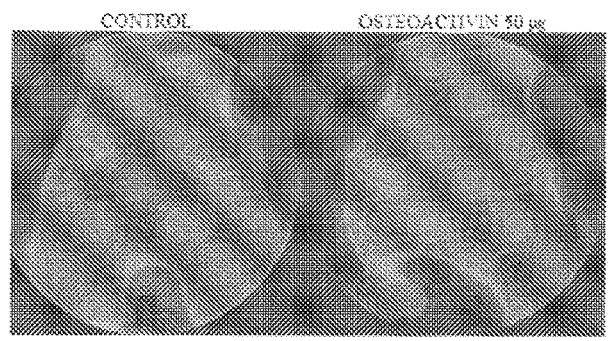
Figure 3A:
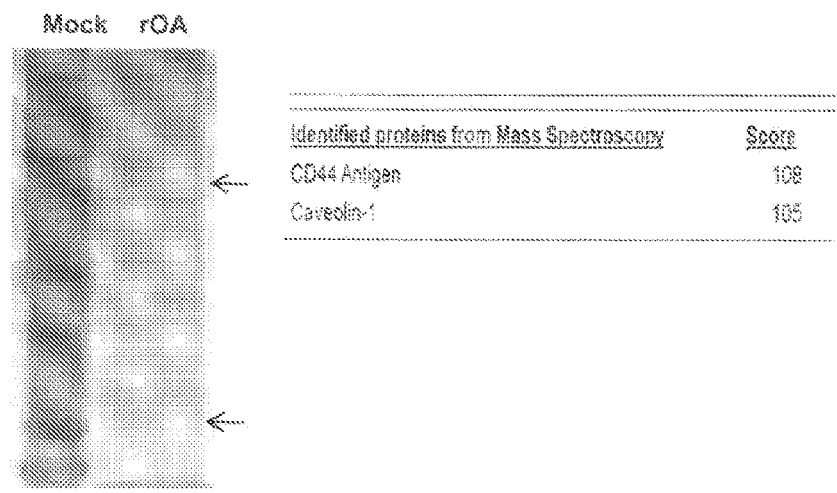
FIG. 3(A-C) provides images showing osteoactivin binds to CD44 in bone cells. (A) Silver staining and mass spectroscopy analysis of biotinylated rOA added onto MC3T3-E1 cells. (B) Immunoflourescence of CD44 and OA reveal colocalization along the cell membrane. (C) Immunoprecipitation of biotinylated rOA onto MC3T3-E1 cells pulled out with streptavidin beads and blotted for CD44 reveals OA-CD44 interaction.
Figure 3B:
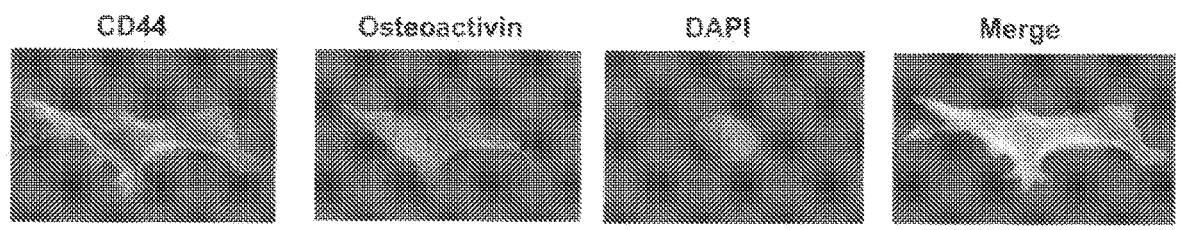
Figure 3C:
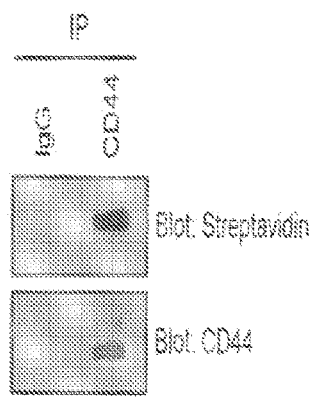

Initial radiographic analysis indicated a complete regeneration of bone at the defect site in both high-dose and low-dose treated sheep, while the control femurs showed no significant change in the size of the defect or significant bone regeneration (see FIG. 1). Micro-CT analysis of control and OA-treated defects measured the bone volume and density of the regenerated area indicating a significant increase at the OA-treated defect sites (see FIG. 2). CBC, CMP and urinalysis showed no apparent abnormalities between control and OA-treated sheep.

Discussion

As a result of this study, it is evident that OA plays a crucial role in bone remodeling and growth following injury in a large animal model. This provides a proof of concept that OA can potentially be utilized as a therapeutic target in accelerating bone regrowth following traumatic injury. Further studies are underway to determine dosing for optimum therapeutic effect and are also needed to compare OA to currently approved osteoinductive compounds such as Bone Morphogenic Protein-2 (BMP-2). Thus far OA has proven to be safe when administered locally with no apparent adverse systemic effects per laboratory studies or histological sampling of the sheep. Our current work indicates feasibility and cause for continued work in assessing OA as a therapeutic target for bone regeneration.

This example shows that OA has promising effects on bone regeneration in a large animal model and can potentially be used as a novel therapeutic agent for a wide variety of patients that would typically require bone grafting but without the inherent side effects.

The complete disclosure of all patents, patent applications, and publications, and electronically available materials cited herein are incorporated by reference. Any disagreement between material incorporated by reference and the specification is resolved in favor of the specification. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A composition for enhancing bone tissue repair or regeneration, comprising a therapeutically effective amount of an active peptide fragment of osteoactivin having the amino acid sequence of SEQ ID NO: 1 and a biocompatible inorganic material configured as a tissue scaffold.

2. The composition of claim 1, wherein the biocompatible inorganic material is an inorganic ceramic and/or bone substitute material.

3. The composition of claim 2, wherein the biocompatible inorganic material is a bone-derived material selected from the group consisting of non-demineralized bone particles, lightly demineralized bone particles, and deorganified bone particles.

4. The composition of claim 1, wherein the biocompatible inorganic material is selected from the group consisting of aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, fluoroapatite, chlorapatite, magnesium-substituted tricalcium phosphate, carbonate hydroxyapatite, and substituted forms of hydroxyapatite.

5. A method for enhancing bone tissue repair or regeneration, comprising: contacting a site in need of bone repair or regeneration in a subject with the composition of claim 1.

6. The method of claim 5, wherein the composition is in an injectable form, and wherein the step of contacting the site comprises administering the composition by injection to the site in need of bone repair or regeneration.

7. The method of claim 5, wherein the step of contacting the site comprises surgically implanting the composition.

8. The method of claim 5, wherein the site in need of bone repair or regeneration is a dental site.

9. The method of claim 5, wherein the biocompatible inorganic material is an inorganic ceramic and/or bone substitute material.

10. The method of claim 9, wherein the biocompatible inorganic material is a bone-derived material selected from the group consisting of non-demineralized bone particles, lightly demineralized bone particles, and deorganified bone particles.

11. The method of claim 5, wherein the biocompatible inorganic material is selected from the group consisting of aragonite, dahlite, calcite, amorphous calcium carbonate, vaterite, weddellite, whewellite, struvite, urate, ferrihydrate, francolite, monohydrocalcite, magnetite, goethite, dentin, calcium carbonate, calcium sulfate, calcium phosphosilicate, sodium phosphate, calcium aluminate, calcium phosphate, hydroxyapatite, alpha-tricalcium phosphate, dicalcium phosphate, β-tricalcium phosphate, tetracalcium phosphate, amorphous calcium phosphate, octacalcium phosphate, fluoroapatite, chlorapatite, magnesium-substituted tricalcium phosphate, carbonate hydroxyapatite, and substituted forms of hydroxyapatite.

* * * * *